(12) United States Patent
Tampieri et al.

(10) Patent No.: US 9,327,027 B2
(45) Date of Patent: May 3, 2016

(54) INTRINSICALLY MAGNETIC HYDROXYAPATITE

(75) Inventors: Anna Tampieri, Faenza (IT); Elena Landi, Dozza (IT); Monica Sandri, Cavriago (IT); Daniele Pressato, Montegrotto Terme (IT); José Rivas Rey, Ames (ES); Manuel Banobre López, Vilarmaior (ES); Maurilio Marcacci, Bologna (IT)

(73) Assignees: CONSIGLIO NAZIONALE DELLE RICERCHE, Rome (IT); UNIVERSIDADE DE SANTIAGO DE COMPOSTELA, Santiago (ES); FIN-CERAMICA FAENZA S.P.A., Faenza (IT)

(*) Notice: Subject to any disclaimer, the term of this patent is extended or adjusted under 35 U.S.C. 154(b) by 12 days.

(21) Appl. No.: 13/812,741

(22) PCT Filed: Jul. 28, 2011

(86) PCT No.: PCT/IB2011/053362
§ 371 (c)(1),
(2), (4) Date: Jan. 28, 2013

(87) PCT Pub. No.: WO2012/014172
PCT Pub. Date: Feb. 2, 2012

(65) Prior Publication Data
US 2013/0129634 A1 May 23, 2013

(30) Foreign Application Priority Data
Jul. 29, 2010 (IT) .............................. MI2010A1420

(51) Int. Cl.
*A61K 47/02* (2006.01)
*A61K 49/08* (2006.01)
(Continued)

(52) U.S. Cl.
CPC ............. *A61K 47/02* (2013.01); *A61K 49/0002* (2013.01); *A61K 49/08* (2013.01);
(Continued)

(58) Field of Classification Search
None
See application file for complete search history.

(56) References Cited

U.S. PATENT DOCUMENTS

| 5,344,640 A | 9/1994 | Deutsch et al. |
| 5,468,465 A | 11/1995 | Deutsch et al. |

(Continued)

FOREIGN PATENT DOCUMENTS

| CN | 101759170 A1 | 6/2010 |
| EP | 0610333 A1 | 8/1994 |
| WO | 9307905 A2 | 4/1993 |

OTHER PUBLICATIONS

Yan Li, et al., "Iron (III) and Manganese (II) Substituted Hydroxyapatite Nanoparticles: Characterization and Cytotoxicity Analysis", Journal of Physics, Conference Series, 187, 2009, pp. 1-8.
(Continued)

*Primary Examiner* — Bethany Barham
*Assistant Examiner* — Dominic Lazaro
(74) *Attorney, Agent, or Firm* — Silvia Salvadori, P.C.; Silvia Salvadori (57) ABSTRACT

The present invention relates to hydroxyapatite doped with $Fe^{2+}$ ions and $Fe^{3+}$ ions which partially substitute the calcium ions in the crystal lattice. The hydroxyapatite is characterized by an intrinsic magnetism of 0.05 to 8 emu/g, measured by applying a magnetic field of 34 Oe, due to the presence of magnetic nano-domains in the crystal lattice of HA, given the limited amount of magnetic secondary phases present, less than about 3% by volume.
The intrinsically magnetic hydroxyapatite can be loaded with biological substances selected in the group consisting of proteins, genes, stem cells, growth factors, vascularization factors, active substances and drugs, under the control of an external magnetic field, as a carrier and release agent for biological substances or drugs, as a contrast agent in diagnostics or for bone or osteocartilage regeneration.

22 Claims, 11 Drawing Sheets

(51) Int. Cl.
*A61L 27/12* (2006.01)
*A61K 49/00* (2006.01)
*A61L 27/54* (2006.01)
*C01B 25/32* (2006.01)
*C01B 25/45* (2006.01)

(52) U.S. Cl.
CPC ............... *A61L 27/12* (2013.01); *A61L 27/54* (2013.01); *C01B 25/32* (2013.01); *C01B 25/322* (2013.01); *C01B 25/45* (2013.01); *A61L 2300/414* (2013.01); *A61L 2300/64* (2013.01); *A61L 2400/12* (2013.01); *A61L 2430/02* (2013.01); *A61L 2430/06* (2013.01); *C01P 2004/62* (2013.01); *C01P 2006/62* (2013.01); *C01P 2006/64* (2013.01)

(56) References Cited

U.S. PATENT DOCUMENTS

| | | | |
|---|---|---|---|
| 5,492,814 A * | 2/1996 | Weissleder | 435/7.25 |
| 5,609,850 A | 3/1997 | Deutsch et al. | |
| 5,690,908 A | 11/1997 | Deutsch et al. | |
| 2005/0272592 A1 * | 12/2005 | Pinnavaia et al. | 502/60 |
| 2009/0074645 A1 | 3/2009 | Wu | |
| 2009/0276056 A1 * | 11/2009 | Bose et al. | 623/23.72 |

OTHER PUBLICATIONS

Wu, et al., "A Novel Biomagnetic Nanoparticle Based on Hydroxyapatite", Nanotechnology, vol. 18, No. 16, 2007, pp. 165601 (9 pages).

Mayer, et al., "Ferric Iron in Synthetic Carbonate Apatites: A Mossbauer Effect Study", Journal of Inorganic Biochemistry, vol. 45, pp. 129-133 (1992).

Jiang, et al., "FE2+/FE3+ Substitution in Hydroxyapatite: Theory and Experiment", Physical Review B, vol. 66, 2002, pp. 224107-1 to 224107-15.

* cited by examiner

INTRINSICALLY MAGNETIC HYDROXYAPATITE

FIELD OF THE INVENTION

The present invention relates to intrinsically magnetic hydroxyapatite and uses thereof in bone and osteocartilage reconstruction, as a carrier for biological substances and/or drugs and as a contrast agent in diagnostics.

BACKGROUND OF THE INVENTION

Hydroxyapatite (HA), $Ca_{10}(PO_4)_6(OH)_2$, is the main mineral component of bone tissue. Given its high biocompatibility and natural affinity for biological substances, hydroxyapatite is commonly used in bone and osteocartilage substitution/regeneration applications and as a carrier for proteins, genes, stem cells, growth factors, active substances, etc.

It is well known that hydroxyapatite has a hexagonal crystal lattice comprising phosphate ions, hydroxyl ions and calcium ions, the latter with hexavalent or tetravalent coordination (positions 6h and 4f).

It is also well known that the structure of hydroxyapatite is capable of accommodating various types of ionic substitutions at the sites of the phosphate ion, hydroxyl ion and calcium ion, without any collapse occurring in the structure.

In other words, hydroxyapatite is a material that can be doped with different types of ions without causing a phase degradation thereof.

In addition to the doping of hydroxyapatite carried out with the aim of enhancing its biomimetic properties in relation to the mineral phase constituting bone tissue, numerous substitutions have been made with ions capable of imparting magnetic properties, such as Fe, Co, Mn and La.

In particular, Mayer et al. (Journal of Inorganic Biochemistry 1992, 45, 129-133) reported the synthesis of hydroxyapatite doped with ferric ions ($Fe^{3+}$HA) using $Fe(NO_3)_3$ as reagent. According to the authors, the ferric ions were not incorporated into the apatite lattice but were present in the apatite itself in the form of Fe-OOH.

Wu et al. (Nanotechnology 2007, 18, 165601-10) reported the synthesis of hydroxyapatite doped with ferrous ions ($Fe^{2+}$HA) using $FeCl_2*4H_2O$ as $Fe^{2+}$ ion source. However, they obtained a product with magnetic properties only in the case in which hydroxyapatite was accompanied by the formation of secondary magnetic phases, such as magnetite.

Ming Jang et al. (Review, Condensed Matter and Materials Physics, 2002, 66, 224107-224115) doped hydroxyapatite with $Fe^{2+}$ and $Fe^{3+}$ ions, starting from $Ca(NO_3)_2$ and $Fe(NO_3)_2$ solutions added drop by drop to an ammonium phosphate solution. The article does not provide any indication as to a possible intrinsic magnetization of the hydroxyapatite.

One of the most relevant limitations connected with the use of scaffolds for bone or osteocartilage regeneration regards the difficulty of controlling the development and speed of the processes of cellular differentiation and angiogenesis at the scaffold implantation site.

These processes are favoured by the speed of migration of bone tissue growth factors and vascularization factors to the implantation site.

Control over the migration of specific factors to the implantation site, according to patient needs and for a prolonged period, is of enormous importance for favouring osseointegration of the prosthesis and the regeneration of the bone tissue, and hence for the healing of the patient.

In this sector, therefore, there is a strongly felt need for a carrier and release system for biological substances and drugs which can enable control of the migration of growth factors, vascularization factors or other biological substances capable of favouring and accelerating osseointegration and bone regeneration. A need is also felt for a drug carrier system which can be guided in a precise and accurate manner so as to release the drug directly, in a selective manner, and according to the real quali-quantitative requirements, only at the site affected by the pathology.

In the sector there also exists a need for a prosthesis for bone and osteocartilage regeneration which is biocompatible at the same time and can be manipulated and constrained in the specific implantation position in vivo by means of a control system outside the patient's body, thus eliminating the present necessity of invasive fixing systems.

SUMMARY OF THE INVENTION

Such needs are solved by an intrinsically magnetic hydroxyapatite and by a method for obtaining it as outlined in the appended claims.

BRIEF DESCRIPTION OF THE DRAWINGS

A detailed description of the invention is set forth below, also with reference to the appended figures, in which.

DETAILED DESCRIPTION OF THE INVENTION

The present invention relates to an intrinsically magnetic hydroxyapatite characterized by a degree of magnetization ranging from 0.05 to 8 emu/g, preferably 0.1 to 5 emu/g, recorded by applying a magnetic field of 34 Oe.

In particular, the hydroxyapatite of the invention is doped with $Fe^{2+}$ and $Fe^{3+}$ ions, which partially substitute the calcium in the crystal lattice.

The $Fe^{3+}/Fe^{2+}$ ratio in the hydroxyapatite lattice ranges from 1 to 4, preferably from 2 to 3.5. The hydroxyapatite of the invention is intrinsically magnetic, i.e. it is endowed with magnetic properties essentially ascribable to the doping of the lattice with $Fe^{3+}$ and $Fe^{2+}$ ions, which substitute (partially) the calcium in an amount, in reciprocal positions, in a relationship of oxidation state/position in the lattice and in specific coordination states such as to generate magnetism.

Without being bound to any theory, it is thought that the magnetism is due to the existence of very small structural domains in the doped HA lattice which resemble the structure of magnetite and are capable of activating the mechanisms responsible for the superparamagnetic property.

XRD analyses and computer simulations on structural models have shown a clear indication that both species of Fe are in calcium substitution positions and not at interstitial sites in the HA lattice.

The Ca(2) position, with a coordination number of 6, and Ca(1) position with a coordination number of 4, are occupied in a reciprocal relationship in such a way as to impart magnetic susceptibility to the powders.

The TEM investigations, as well as the magnetic measurements, confirmed the presence of a new magnetic phase of HA together with nanoclusters similar to magnetite. This new phase is a distorted/disordered hydroxyapatite with $Fe^{2+}$, in its nominal divalent state, and $Fe^{3+}$, which has a deviation from its nominal trivalent state, organized on a surface and bulk level and coordinated to generate magnetism in the HA itself.

The hydroxyapatite of the invention can comprise an amount of secondary magnetic phases (e.g. magnetite type secondary phases) below about 3% by volume. Preferably, the amount of secondary magnetic phases is ≤2% by volume.

The low amount of secondary phases present alongside the hydroxyapatite of the invention indicates that the majority of the iron ions used for doping substitute calcium in the HA lattice and only a small part of them contribute to the formation of iron oxides (like magnetite) which have magnetic properties.

In virtue of the low amount of secondary magnetic phases, e.g. magnetite, the doped hydroxyapatite of the invention maintains the good biocompatibility characteristics typical of non-doped hydroxyapatite. In fact, the higher the amount of secondary magnetic phases, the lower the biocompatibility of hydroxyapatite.

The hydroxyapatite of the invention preferably has a (Fe+Ca)/P ratio ranging from 1.5 to 1.9. Such values come near the value of the Ca/P ratio in non-doped HA.

Values of the (Fe+Ca)/P ratio ranging from 1.5 to 1.9 indicate that doping with iron ions as substitutes for calcium has not brought about large alterations in the chemical structure of the material, which, even after doping, retains the chemical-structural characteristics typical of non-doped hydroxyapatite. The doped hydroxyapatite of the invention is preferably in the form of particles (or nanoparticles) having dimensions of 5-10 nm to 20-30 nm in width and up to 80-150 nm in length. The particles may contain spherical voids of 2-5 nm.

The intrinsically magnetic hydroxyapatite of the invention is synthesized with a method comprising the steps of:
a) adding a solution comprising Fe(II) and Fe(III) ions to a suspension/solution containing Ca(II) ions;
b) heating the suspension of step a) to a temperature in the range of 15° C. to 80° C.;
c) adding a solution of phosphate ions to the suspension/solution of step a);
d) separating the precipitate from the mother liquors.

Preferably, said Fe(II) and Fe(III) ions derive, respectively, from $FeCl_2$ and $FeCl_3$.

Preferably, said Ca(II) ions derive from calcium hydroxide, calcium nitrate, calcium acetate, calcium carbonate and/or other calcium salts.

The solution of phosphate ions is added to the suspension/solution containing calcium ions and iron ions in a period of 1-3 hours, preferably by heating and stirring the suspension. Preferably, the phosphate ions derive from phosphoric acid and/or soluble salts thereof.

The amount of iron ions used is such as to obtain an Fe/Ca molar ratio ranging from 5 to 30, preferably 10 to 20 mol %.

On completion of this step, the suspension can be maintained under constant stirring for 1-2 hours and then allowed to rest, without stirring or heating, for 12-36 hours.

In this way a precipitate is obtained which is separated from the mother liquors, preferably by centrifugation.

The separated precipitate is subsequently dispersed in distilled water and centrifuged at least three times.

Preferably, the precipitate is washed at least three times, freeze dried and sieved.

The subject matter of the invention also relates to an intrinsically magnetic hydroxyapatite, preferably, in the form of intrinsically magnetic nanoparticles, obtainable with the method of synthesis described above.

The intrinsically magnetic hydroxyapatite of the invention is a material which retains a biocompatibility wholly comparable to that of non-doped hydroxyapatite and can thus be used for different purposes in the clinical and/or diagnostic sectors.

In particular, the intrinsically magnetic hydroxyapatite can be used as a carrier and release agent for biological factors or drugs, as a contrast agent in diagnostics or else as a bioactive magnetic substitute for bone and osteocartilage regeneration.

As regards its use in the diagnostic sector, the intrinsically magnetic hydroxyapatite of the invention can be used as a contrast agent, for example in magnetic resonance imaging (MRI). In this case, once the magnetic hydroxyapatite has been suitably functionalized (for example with specific antibodies capable of locating themselves in predetermined regions of the body, e.g. in a tumour), it is administered to the patient and, by applying an external magnetic field of suitable intensity, it is possible to locate the particles and thus detect whether any pathological alterations are present or not.

Another use of the hydroxyapatite of the invention is as a carrier and release agent for active substances, for example antitumour drugs and/or antibiotics for selective treatment at the pathological site. In this case, once administered, the magnetic hydroxyapatite particles can be guided, by applying a suitable magnetic field, toward the pathological site, where they will release the active ingredient they are carrying.

In this manner a system is created for carrying and releasing drugs in a controlled manner, in terms of speed and selectivity of release.

For the treatment of tumours it is possible to use the magnetic hydroxyapatite particles of the invention in order to locally increase the temperature (magnetothermia or hyperthermia). In practical terms, once administered to the patient, the hydroxyapatite particles (devoid of any active substance) can be guided, by applying a magnetic field, toward the tumour site. Once they have reached the site the temperature can be increased by applying suitable magnetic fields, in such a way as to provoke tumour cell necrosis.

Another use of the hydroxyapatite particles of the invention is as a carrier and release system for biological agents, in particular proteins, genes, stem cells, growth factors and vascularization factors; the system can be guided, by applying an external magnetic field, towards an implanted magnetic bone substitute (for example made of the same magnetic hydroxyapatite), or toward a non-magnetic implanted scaffold.

In this manner, one may influence the speed of osteointegration of the implanted bone and/or osteocartilage substitute, and tissue regeneration, by increasing as necessary, according to individual patient needs, the amount of growth and vascularization factors at the site where difficulties in the healing process are detected. Increasing the amount of such factors can be achieved by applying an external magnetic field which enables the particles of the invention to be guided towards the site where bone or osteocartilage regeneration proves to be particularly difficult.

The subject matter of the invention, therefore, is an intrinsically magnetic hydroxyapatite having the above-described physicochemical characteristics, loaded with biological substances selected from among: proteins, genes, stem cells, growth factors, vascularization factors, and active substances or drugs. Said hydroxyapatite is preferably in the form of intrinsically magnetic nanoparticles.

All of the above-described uses are based on the principle of being able to control the internal distribution of the carrier and release system from a remote location, by applying an external magnetic field. The intrinsically magnetic hydroxyapatite particles can thus be defined as nanodevices for carrying and releasing biological and pharmacological substances.

The major advantage of the hydroxyapatite of the invention resides in its high biocompatibility, which is comparable with the biocompatibility of non-doped hydroxyapatite and superior to that of systems consisting of hydroxyapatite plus secondary magnetic phases. The carrier and release system of the invention thus does not require, unlike the magnetic carrier and release systems known in the art, any further modifications (e.g. the application of coatings) aimed at enhancing the biocompatible properties thereof.

In fact, the known magnetic particles have a magnetic core protected by various monolayers of inert material, e.g. silica. Alternatively, organic/biological substances can also be used; these can be adsorbed onto the surface of the magnetic particles in such a way to form a biocompatible coating.

Examples of organic/biological coatings include antibodies and biopolymers (such as collagen), or monolayers of organic molecules which render the magnetic particles biocompatible. Furthermore, the substances to be delivered must be linked to the known magnetic particles by means of a linker with reactive groups at both ends.

One functional group serves to connect the linker to the surface of the particles, whereas the second functional group is used to bind the molecules to be carried.

The advantage of the hydroxyapatite particles of the invention is that they are intrinsically magnetic and intrinsically biocompatible without the necessity of applying further layers of organic/inorganic material to enhance that property. Moreover, the substances to be carried can be directly loaded onto the hydroxyapatite without the necessity of employing a linker substance.

Another use of the magnetic hydroxyapatite of the invention is for the preparation of three-dimensional biomimetic constructs to be used as bone or osteocartilage substitutes in bone or osteocartilage regeneration applications.

These magnetic biomimetic scaffolds can be constrained in a given position in vivo by using suitable magnetic forces applied from the outside. Moreover, such scaffolds can be biologically manipulated in situ by applying a suitable external magnetic field which makes it possible to guide other particles of magnetic hydroxyapatite according to the invention, loaded with growth factors, vascularization factors, stem cells, drugs or, in any case, biological agents, towards the magnetic device, so as to release the above-mentioned substances in situ according to the quali-quantitative and time requirements of the patient. Therefore, the subject matter of the invention further relates to a 3D biomimetic device, in particular for use in bone or osteocartilage regeneration, comprising particles, preferably nanoparticles, of intrinsically magnetic hydroxyapatite according to invention.

EXAMPLES

Magnetic and biomimetic hydroxyapatite (HA) powders were prepared using $FeCl_2$ and $FeCl_3$ as sources of $Fe^{2+}$ and $Fe^{3+}$ doping ions. Three different methods of synthesis from the aforesaid salts were compared; they are described in detail in examples 1-3.

The chemical composition, structure and magnetic properties of the synthesized Fe-HA powders were determined with the following methods.

The chemical analysis was performed by inductively coupled plasma optical emission spectrometry (ICP-OES; Liberty 200, Varian, Clayton South, Australia): 20 mg of powder was dissolved in 2 ml of $HNO_3$ and the volume of solution was raised to 100 ml by adding deionized water.

The amount of $Fe^{2+}$ was confirmed by means of UV-Vis spectrophotometric analysis, exploiting the ability of $Fe^{2+}$ ions to form complexes with ortophenantroline determinable at 510 nm. The amount of $Fe^{3+}$ was determined by calculating the difference between the total amount of iron (determined with ICP) and the amount of $Fe^{2+}$ (determined with UV-VIS).

Morphological evaluation of the powders was performed with a scanning electron microscope (SEM; Stereoscan 360, Leica, Cambridge, UK).

Determination with backscattered electrons (BSE) was used to qualitatively visualize the Fe distribution in the powders. EDS (energy dispersive spectroscopy, Link Oxford) was used for semi-quantitative chemical analysis.

X-ray diffraction analysis (CuKa radiation; Rigaku Geigerflex, Tokyo Japan) was employed to determine the crystal phases present and estimate the degree of crystallinity of the powder. A transmission electron microscope (JEOL TEM 3010-UHR, Japan, 300 kV) was used to observe the characteristics of the material on a nanoscale level.

The magnetism of the powders was measured in a low field (34 Oe) with a YSZ 01C/02C susceptometer (Sartorius Mechatronics, Italy).

Magnetic measurements were also performed using a Superconducting Quantum Interference Device (SQUID) magnetometer (Quantic Design) capable of operating from 1.8K to 350K in a maximum applied magnetic field of H=5T (50000 Oe).

In this case a few milligrams of sample in powder (20 mg) were measured from 5K to 300K in an applied magnetic field of H=100 Oe so as to obtain the M (magnetism) vs. T (temperature) curves, while the M vs. H curves (magnetic field intensity) were measured in a single magnetic field cycle from 2T to −2T (+/−20000 Oe) at T=300K.

Synthesis Example 1 (for Comparison)

Maintaining the general synthesis procedure described previously, one method of synthesis consists in adding solely $FeCl_3$ as a source of $Fe^{3+}$ ions, subsequently partially reduced to $Fe^{2+}$ ions so as to obtain an $Fe^{3+}/Fe^{2+}$ ratio equal to about 3.

Figure 2:
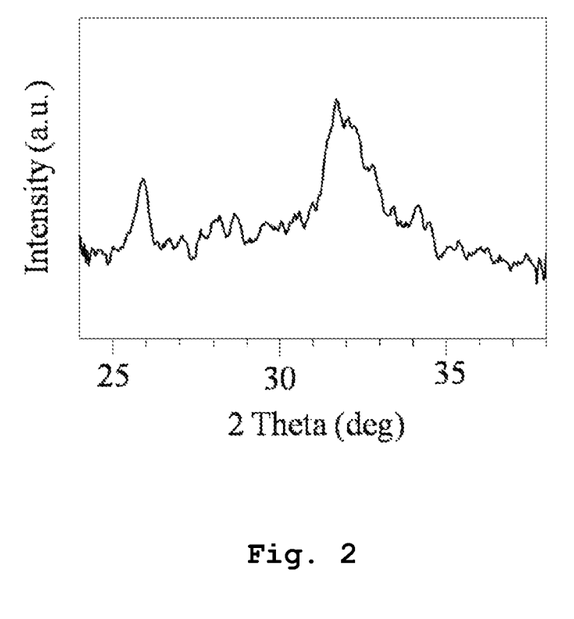
FIG. 2 shows the XRD analysis of an HA sample synthesized in the presence of $Fe^{3+}$ ions at 40° C. (Fe/Ca ratio=0.20)

The powders synthesized by adding $Fe^{3+}$ ions, adopting an initial Fe/Ca molar ratio of 0.20, and a temperature of 40° C., show a considerable distortion in the HA lattice, as revealed by XRD diffractometric analysis; however, no secondary phases were detected (FIG. 2).

The synthesized powder not subjected to a reduction process showed no sign of magnetization, as was expected given that iron is present only in its highest oxidation state.

The powder was then subjected to a reduction process. The reduction process was carried out in a closed autoclave (Parr, Alloy C276), using $H_2$ (4%) in 96% Ar as the reducing gas at different pressures. Table 1 summarizes the experimental autoclave reduction conditions for the $Fe^{3+}$HA powder.

TABLE 1

| Sample | $T_{red}$ [° C.] | Time [min] | Stirring | P [psi] |
|---|---|---|---|---|
| A | 300 | 60 | NO | 270 |
| B | 300 | 60 | YES | 270 |
| C | 300 | 60 | YES | 400 |

The characteristics of the reduced powders are given in Table 2, which shows the relationship between magnetism and the $Fe^{3+}/Fe^{2+}$ molar ratio calculated for the reduced $Fe^{3+}$ HA sample.

TABLE 2

| Reduced sample | $Fe^{2+}$(HA) [wt %] | $Fe^{3+}$(HA) [wt %] | $Fe^{3+}/Fe^{2+}{}_{(HA)}$ | Magnetization [emu/g] |
|---|---|---|---|---|
| A | 5.5 | 4.9 | 0.89 | 0.00122 |
| B | 7.3 | 3.1 | 0.42 | 0.00108 |
| C | 9.6 | 0.8 | 0.08 | 0.00128 |

Very low magnetization values were recorded for all synthesized powders. In fact, one may hypothesize a preferential reduction of the $Fe^{3+}$ ions present on the surface, accompanied by a non-homogeneous reduction of the bulk, which leads to the formation of an excessive amount of $Fe^{2+}$ ions. The reduction method applied seems to be characterized by reaction conditions that are too extreme for obtaining a balanced distribution of $Fe^{3+}/Fe^{2+}$ ions in the HA lattice.

In fact, the concentration of $Fe^{2+}$ determined by UV-Vis spectrophotometric analysis, exploiting the capacity of $Fe^{2+}$ ions to form a complex with ortophenantroline, showed to be very high, thus excessively decreasing the $Fe^{3+}/Fe^{2+}$ ratio (Table 2).

Synthesis Example 2 (for Comparison)

Maintaining the general synthesis procedure described previously, an alternative method of synthesis envisages adding solely $FeCl_2$ as the source of $Fe^{2+}$ ions. The latter undergo spontaneous oxidation to $Fe^{3+}$ ions under the reaction conditions. Powders were synthesized by adding $Fe^{2+}$ ions, adopting an initial Fe/Ca molar ratio of 0.20, and diversifying the temperature of synthesis (25° C., 40° C., 60° C.)

The experimental reaction conditions and the properties of the powders obtained as a result are given in Table 3

TABLE 3

| Sample | Conditions of synthesis | $Fe_3O_4$ [vol %] | $Fe_{(tot)}$ [wt %] | $Fe^{2+}{}_{(HA)}$ [wt %] | $Fe^{3+}/Fe^{2+}{}_{(HA)}$ | $(Fe + Ca)/P_{(HA)}$ | M [emu/g] |
|---|---|---|---|---|---|---|---|
| D | $Fe^{2+}$ T: 25° C. Fe/Ca = 0.20 | 0.00 | 9.10 | 1.30 | 5.99 | 1.728 | 0.006 |
| E | $Fe^{2+}$ T: 40° C. Fe/Ca = 0.20 | 3.00 | 8.81 | 1.03 | 4.13 | 1.716 | 0.339 |
| F | $Fe^{2+}$ T: 60° C. Fe/Ca = 0.20 | 5.50 | 8.72 | 2.79 | 0 | 1.601 | 0.558 |

Figure 3:
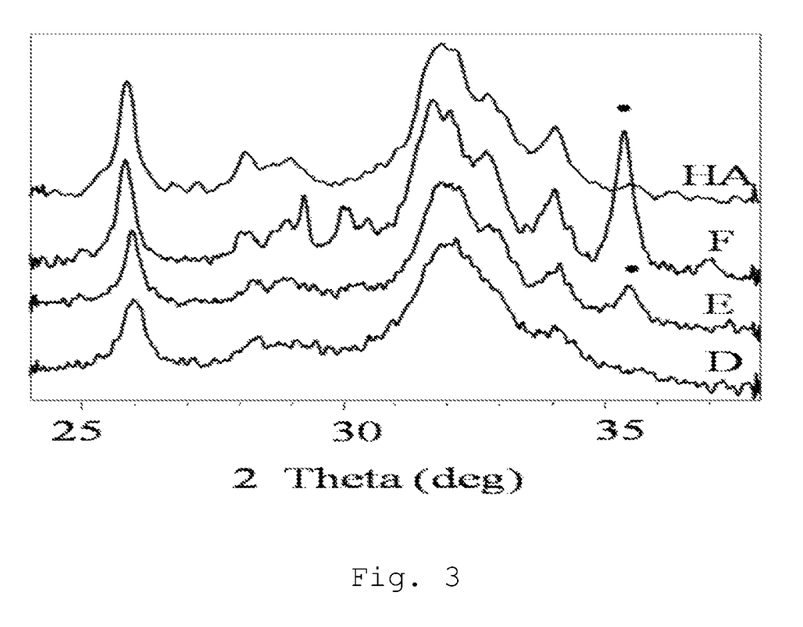
FIG. 3 shows the RX diffractograms of non-doped HA and HA synthesized by adding $Fe^{2+}$ ions (Fe/Ca=0.20) at different temperatures [D=25° C.; E=40° C.; F=60° C.]; the peaks marked with the symbol • correspond to the magnetite phase ($Fe_3O_4$)

The XRD diagram in FIG. 3 shows the magnetite peak at $2\theta\sim36°$ in samples E and F, whereas the resolution pattern in the spectrum of sample D decreases as expected, since it was prepared at a lower temperature.

The characteristics of the powders are closely dependent upon the process of synthesis, as shown in table 3.

The formation of magnetite is favoured at a higher temperature (60° and 40° C.) and under these conditions the magnetic value increases thanks mainly to the contribution of magnetite, which forms alongside the Fe-substituted HA. At 25° C. the formation of magnetite is minimized and the iron ions enter the lattice in greater number, as demonstrated by the distortion of the same (FIG. 3). The total amount of iron ions determined by ICP (Table 3) corresponds to the nominal concentration of $FeCl_2$ introduced in all samples. The $Fe^{3+}/Fe^{2+}$ ratio is calculated using the amount of $Fe^{2+}$ determined with UV and the amount of $Fe^{3+}$ obtained by subtracting the amount of $Fe^{2+}$ from the total iron content determined with ICP, in both cases after subtracting the contribution of $Fe^{2+}$ and $Fe^{3+}$ ions which form magnetite. As shown in table 3, the $Fe^{3+}/Fe^{2+}$ ratio is very high for samples D and E. As the reaction temperature increases (sample F), the amount of magnetite as a secondary phase likewise increases, and the amount of $Fe^{3+}$ available to enter the HA lattice decreases.

The magnetization value of sample D is very low since: i) magnetite, as a secondary phase, is absent; ii) both species of iron ions enter the lattice but the $Fe^{3+}/Fe^{2+}$ ratio is very high and the distribution of $Fe^{2+}$ and $Fe^{3+}$ ions and their coordination states are not appropriate.

In samples E and F the high magnetism value is essentially ascribable to the concentration of magnetite.

Synthesis Example 3 (of the Invention)

$FeCl_2$ and $FeCl_3$ are added simultaneously to the calcium hydroxide suspension in $Fe^{3+}:Fe^{2+}$ ratios of 1:1.

A solution of phosphoric acid (Aldrich 85% wt) is added to the suspension containing dispersed calcium hydroxide (Aldrich 95% wt) and iron ions for a period of about 1-2 hours with constant heating and stirring. The synthesis reaction is conducted at 40° C. The amounts of iron chloride are such as to produce initial Fe/Ca molar ratios=0.10 and 0.20.

The reaction product is maintained in suspension by constant stirring and heating for 1 hour and then left for 24 hours without heating or stirring.

The precipitate obtained, which is brown in colour, is separated from the mother liquors by centrifugation and then washed and centrifuged three times.

The precipitate is subsequently freeze dried and sieved at 150 µm.

Figure 4:
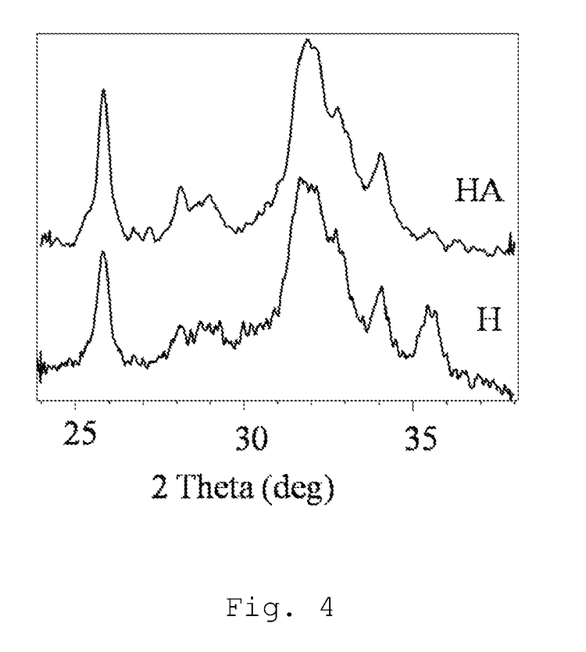
FIG. 4 shows the XRD pattern of non-doped HA and HA produced by adding $Fe^{3+}$ and $Fe^{2+}$ ions (Fe/Ca=0.20) synthesized at 40° C. (H)

The addition of both reagents ($FeCl_2$ and $FeCl_3$) makes $Fe^{2+}$ and $Fe^{3+}$ simultaneously available during HA nucleation: under these conditions the amount of magnetite that forms is smaller compared to the comparative methods described above. The XRD spectrum in FIG. 4 shows that the simultaneous addition of $Fe^{2+}$ and $Fe^{3+}$ causes a strong disturbance in the HA lattice, making it very difficult to evaluate the lattice parameters.

Table 4 shows the relationship existing between the reaction conditions and the characteristics of $Fe^{2+}Fe^{3+}HA$.

TABLE 4

| Sample | Conditions of synthesis | $Fe_3O_4$ [vol %] | $Fe_{(tot)}$ [wt %] | $Fe^{2+}_{(HA)}$ [wt %] | $Fe^{3+}/Fe^{2+}_{(HA)}$ | $(Fe + Ca)/P_{(HA)}$ | M [emu/g] |
|---|---|---|---|---|---|---|---|
| G | $Fe^{3+} + Fe^{2+}$ T: 40° C. Fe/Ca = 0.10 | 1.50 | 4.92 | 0.71 | 3.41 | 1.750 | 0.476 |
| H | $Fe^{3+} + Fe^{2+}$ T: 40° C. Fe/Ca = 0.20 | 2.00 | 9.93 | 1.82 | 3.15 | 1.678 | 0.679 |

The high magnetization value of sample H (Table 4) cannot be justified by the sole contribution ascribable to magnetite. The high magnetization can therefore be attributed to the optimal ratio between iron ions ($Fe^{3+}/Fe^{2+}=3.15$) and the specific relative position and coordination of the two oxidation states of iron.

These results suggest the existence of very small structural domains in the HA lattice which simulate the structure of magnetite and are capable of activating the mechanisms responsible for the superparamagnetic property.

The analysis showed an amorphous Ca—P phase which contains iron oxide particles in a very low concentration. The phase under the beam is very unstable, also due to the high degree of amorphism.

The iron content determined with the EDS probe is 15-20%, probably present in the HA lattice or in very small clusters of less than 1-2 nm.

Figure 5:
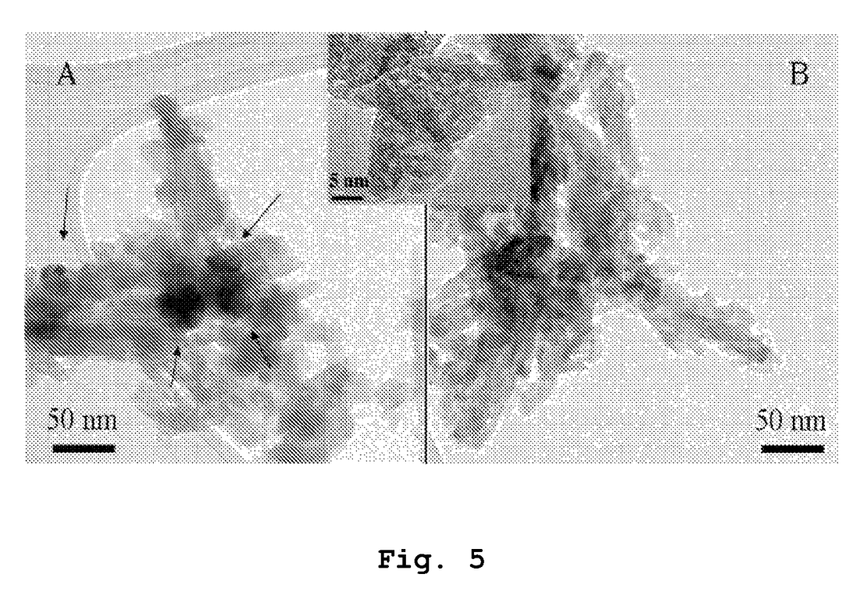
FIGS. 5A and 5B show low-resolution TEM images of sample E (the black arrows indicate the magnetite particles) and sample H, respectively; the box in common contains the amplified TEM image, which shows the presence of nano-voids in the two samples.

Micrographs typical of samples E and H are shown in FIG. 5. The particles mainly exhibit an elongated morphology, fairly homogeneous in size, from 5-10 nm to 20-30 nm in width and up to 80-150 nm in length, and may contain spherical voids of 2-5 nm. In the case of sample E, the magnetite is in the form of nanoparticles having dimensions of 10-30 nm.

Figure 6:
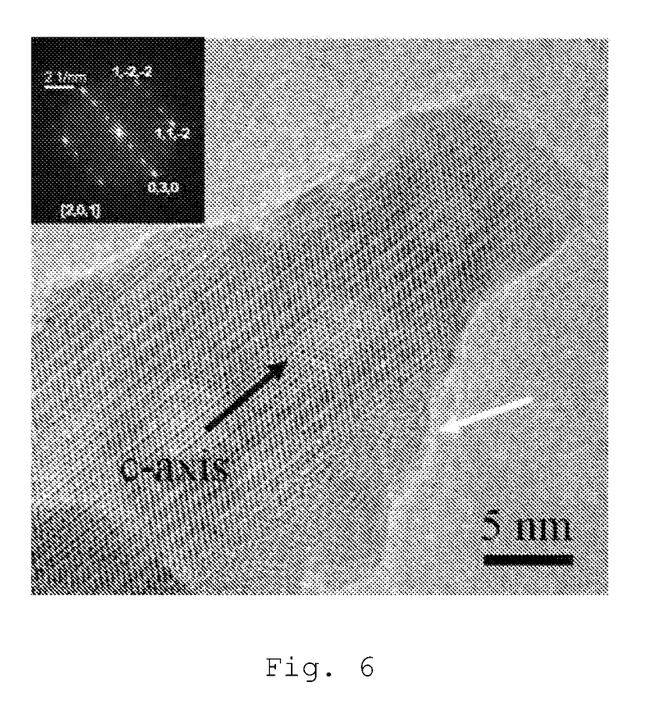
FIG. 6 presents a high-resolution detail of a TEM micrograph which shows a representative particle of sample E or H observed along the axes [2,0,1] of HA; the black arrow indicates the orientation of the c axis of the HA lattice obtained from the Fourier transform of the image (box) and the white arrow points toward an amorphous region of the particle.

HRTEM analysis (FIG. 6) revealed that a part of the material is made up of both amorphous domains and crystal domains of HA, elongated in the direction of the C axis, which can also coexist in the same particle (see FIG. 6 and corresponding detail). The total content of iron, calcium and phosphorous in the calcium phosphate phase was measured for both powders E and H using EDS/TEM (carefully choosing, in the case of sample E, the regions in which magnetite was not present). The results in the form of molar ratios between the elements present (table 5) are consistent with those obtained by means of ICP, XRD and UV-vis as previously reported (Table 4).

Table 5 shows the results of quantitative EDS/TEM analysis of samples E and H and the same samples treated at 700° C. (Et and Ht).

TABLE 5

| Sample | $Fe_{(CaP)}/Ca$ | $(Ca + Fe)/P_{(CaP)}$ |
|---|---|---|
| E | 9 ± 1.5 | 1.5 ± 0.1 |
| $E_t$ | 18 ± 3 | 1.5 ± 0.1 |
| H | 20 ± 0.5 | 1.6 ± 0.1 |
| $H_t$ | 16 ± 1 | 1.4 ± 0.1 |

Since no evidence was found of the presence of an iron-rich phase, not even in powder H (in which the initial molar ratio of Fe to calcium is $Fe_{tot}/Ca(HA)=0.20$), it is presumed that the iron ions are distributed homogeneously and preponderantly in substitution of the $Ca^{2+}$ ions of the HA lattice or in the amorphous phase as very small clusters (<1 nm).

Indirect evidence of the homogeneous distribution of the iron ions can be derived from the behaviour of the samples exposed to relatively large doses of electrons. Under these conditions, in fact, the materials are highly unstable: the voids collapse rapidly and the particles undergo morphological changes accompanied by structural rearrangements and part of the material is transformed into CaO.

Figure 7:
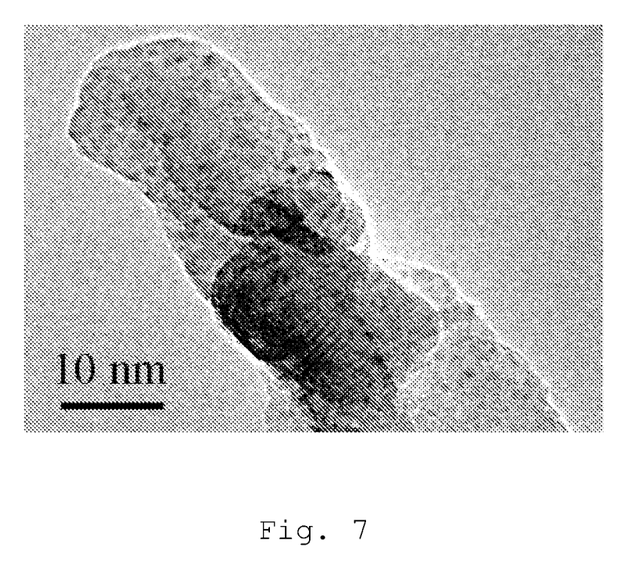
FIG. 7 presents a TEM image showing a particle of sample E after radiation damage; the darker regions of the image correspond to an iron-rich nanophase.

It is interesting to note that, after a few seconds, new particles with a diameter of 1-1.5 nm are formed (see FIG. 7). The new phase which forms is an iron-rich compound, probably originating from the coalescence of iron ions or clusters during the process of damage that occurs as a result of bombardment with electrons.

Figure 8:
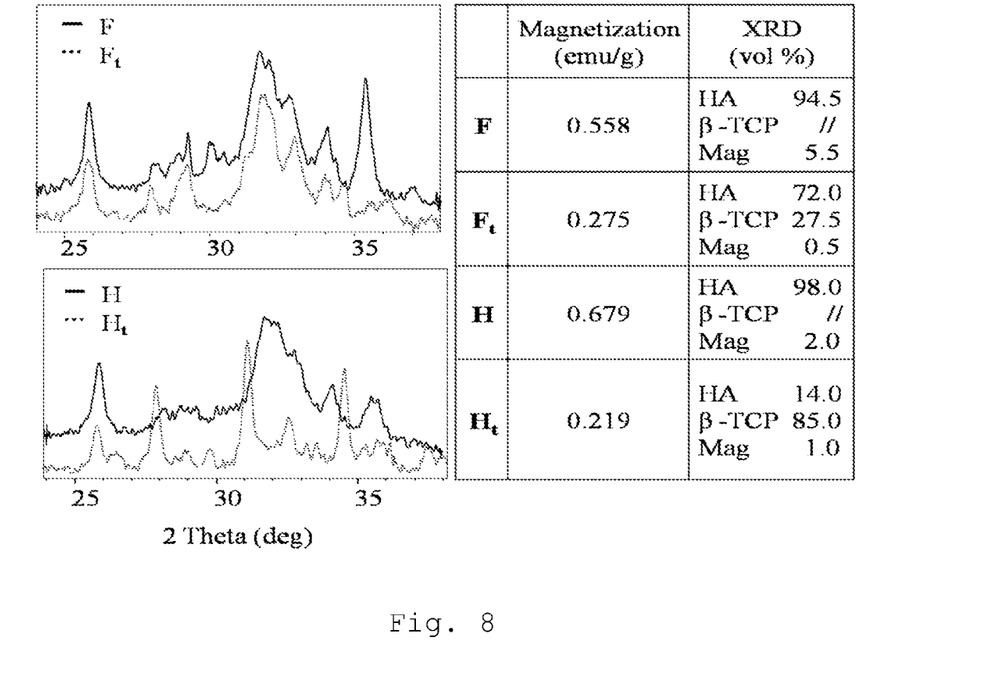
FIG. 8 shows the relation between the magnetization values and XRD patterns obtained for samples E and H.

A heat treatment at 700° C. for 1 hour in an Ar atmosphere is subsequently applied to powders E and H. The resulting XRD spectra are shown in FIG. 8.

Sample E containing large quantities of magnetite showed to be fairly stable and following the heat treatment (Et) the amount of HA remained about 72%.

Since the secondary phase β-TCP $Ca_3(PO_4)_2$ is formed (26%), while the magnetite almost disappears, it is supposed that both iron ions enter the STCP lattice, forming $Ca_9Fe(PO_4)_7$ and $Ca_9FeH(PO_4)_7$. In the case of sample H (which is assumed to be made up of HA whose lattice is partially occupied by $Fe^{2+}$ and $Fe^{3+}$, which form magnetically active microdomains), the thermal stability is much lower. This proves the high disturbance of the crystal structure due to the simultaneous occupation by both iron ions (Ht).

Figure 9:
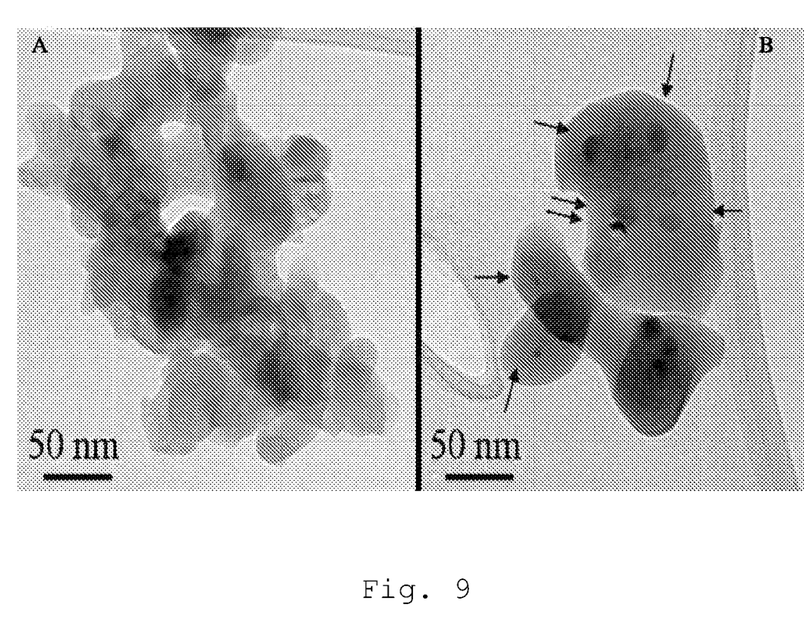
FIGS. 9A and 9B show low-resolution TEM images of materials treated at 700° C.: A) sample $E_t$; B) sample $H_t$ (the arrows indicate an iron-rich phase)

TEM micrographs of samples (Et) and (Ht) are shown in FIG. 9. Sample (Et) shows particles with very irregular spheroid shapes having a width of about 30-50 nm and variable length, obtained by sinterization of the primary particles of the starting powders.

The sample is characterized by a uniform contrast, indicative of a homogeneous dispersion of the iron.

HRTEM analysis confirmed that the calcium phosphate phase is principally of the HA type, with some volume fractions of β-TCP, and revealed that a narrow fraction of the material consists of a pure phase which shows an amorphous character, probably deriving from the magnetite particles which lose their structure as a result of the heat treatment.

In this case as well, even though the sample is more resistant to damage by the beam, after the calcium phosphate is exposed to large doses of electrons, new small particles appear, indicating the presence of very small clusters of iron species in the undamaged HA or in the β-TCP lattice. It is interesting to observe that the iron content measured ($Fe_{tot}/Ca$ (HA)) in the calcium phosphate is about 18±3% (see table 5), more than double that of the starting powders. This indicates that the heat treatment promotes the diffusion of iron species from the magnetite to the calcium phosphate. This, together with the amorphization of the magnetite, explains the disappearance of magnetite peaks observed in the RX diffractogram (FIG. 8).

On the other hand, the particles of sample (Ht) are larger and more spherical (without voids on the inside) and exhibit evident contrast variations (FIG. 9) associated with the presence of an iron-rich phase, which is not observed in the starting powders.

The HRTEM and EDS analyses together confirm that the calcium phosphate is present for the most part in the form of B-TCP substituted with iron, which encapsulates oxide and amorphous iron particles.

The Fe/Ca ratio measured (in regions in which no pure iron oxide is present) is about 16±1%, lower than in the starting powders.

Physicochemical and Magnetic Characterization

Figure 1:
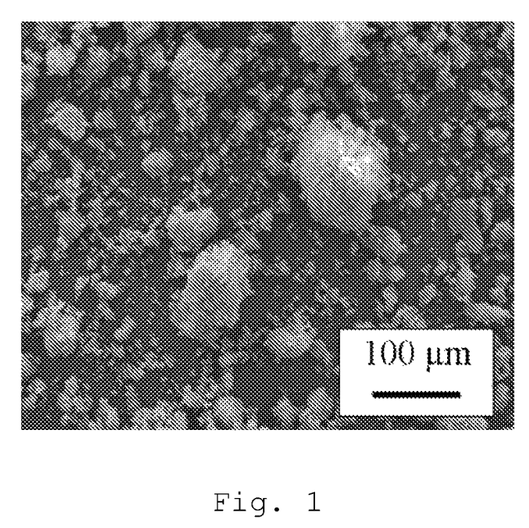
FIG. 1 shows the morphology of an HA sample substituted with iron ions

The powders obtained were brown in colour and characterized by agglomerates with dimensions of about 30-60 μm, as shown in the SEM image in FIG. 1.

The XRD diffractogram patterns appear to be very broad; this is indicative of a considerable distortion of the HA lattice; in any case, no secondary phosphate phases were detected alongside HA.

With the aid of computer simulations on structural models, a clear indication was obtained that the Fe ions are not at an interstitial site in the hydroxyapatite lattice, but are rather substitutes for the Ca ions (with small difference between the tetra- and hexacoordinate lattice positions 4f and 6h).

ICP analysis confirmed the presence of iron in the powder, in an amount equal to the nominal amount introduced; the Ca/P ratio was lower than the theoretical one due to the depletion of calcium.

It is supposed that corresponding amounts of iron as $Fe^{3+}$, $Fe^{2+}$ and ($Fe^{3+}+Fe^{2+}$) substitute Ca, since the $(Fe_xCa)/P$ ratio approaches the theoretical value.

BSE analysis confirmed a homogeneous distribution of iron in the powder; microprobe analysis was also able to detect the same nominal amount of iron added during the reaction.

Figure 10:
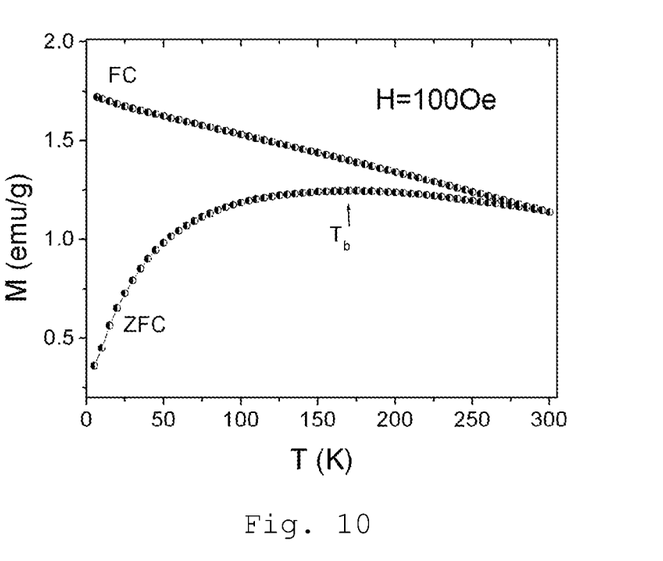
FIG. 10 shows magnetic ZFC-FC curves for sample H at an applied magnetic field of 100 Oe; the arrow indicates the blocking temperature ($T_B$)

The magnetic properties under a high magnetic field were measured using a SQUID magnetometer (Quantum Design). Evidence of the presence of an intrinsically magnetic phase in the hydroxyapatite lattice was found for sample H. FIG. 10 shows the dependency of magnetization on temperature under zero-field-cooled (ZFC) and field-cooled (FC) conditions from 5K to 300K, in an applied magnetic field of 100 Oe. Both curves show the typical behaviour of a system of interacting magnetic particles with an average blocking temperature of TB=170K. TB is significantly high, probably due to the presence of aggregates of smaller magnetite nanoparticles (~10 nm), which act as a secondary phase (in accordance with other characterization techniques, which confirm the presence of 2% vol of magnetite as a secondary phase outside the hydroxyapatite lattice) and separate the state blocked by the superparamagnetic state. Below TB the free movement of the magnetic moment of the particles is blocked; above TB, the thermal energy induces rapid fluctuations in the magnetic moment of the entire particle in relation to the time of observation, such as to make the system appear superparamagnetic. TB is closely correlated with interparticle dipolar interactions and increases with increasing dipolar interactions.

As a consequence of the formation of aggregates, the local concentration of nanoparticles, and thus the force of the interparticle dipolar interactions, increases, modifying the energy barrier for magnetic relaxation and determining the overall magnetic behaviour of the samples.

Figure 11:
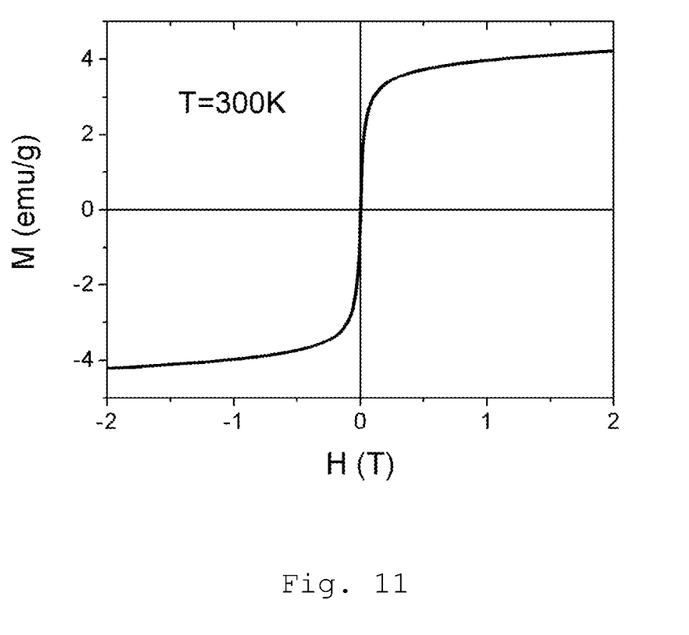
FIG. 11 shows the magnetism as a function of the magnetic field applied at 300K for sample H.

FIG. 11 shows the magnetization curves as a function of the magnetic field applied, from −2 to 2 Tesla, at 300K for sample H.

One may clearly observe the typical superparamagnetic (SPM) behaviour of single-domain magnetic nanoparticles, which indicates that the particle size is below the magnetic multidomain range (25-30 nm for magnetite). This is consistent with the TEM micrographs shown in FIG. 5B, where magnetite aggregates of about 5-10 nm can be noted. On the other hand, the saturation magnetization (Ms) of the sample is significantly low (about 4-5 emu/g) and the secondary phase identified in the form of magnetite nanoparticles (which represents 2% vol) is not sufficient to justify the value of magnetization observed. Therefore, two different magnetic contributions are responsible for the total magnetization in the material: one obviously comes from the magnetite nanoparticles and the other from the hydroxyapatite particles substituted with $Fe^{2+}$ and $Fe^{3+}$ ions.

In the case of the former, the origin of the magnetism is known, whereas in the latter the magnetism derives from the partial substitution of specific $Ca^{2+}$ sites in the HA lattice with magnetic $Fe^{2+}$ and $Fe^{3+}$ ions.

With the aim of finding the structural and magnetic phase responsible for the magnetism in the hydroxyapatite lattice, the common magnetization of a system of magnetite nanoparticles (ø~10 nm, Ms~60-80 emu/g) was subtracted from the total normalized saturation magnetization (Ms~4-5 emu/g). In this manner it was possible to determine the magnetization associated with iron-substituted HA alone. In any case, this calculated Ms is greater than foreseen, also where the total Fe mass in the material (6-7% by weight) is present as magnetite.

Therefore, the magnetic data found support the assumption that the Ms value is caused by the presence of structural magnetic domains (similar to magnetite and/or other iron oxides) in the hydroxyapatite lattice.

In Vitro Tests

Preliminary cell adhesion and biocompatibility tests were conducted on granulated HA and magnetic HA powders using mesenchymal stem cells (MSC), which, after characterization, were cultured in a controlled atmosphere (5% $CO_2$; T=37° C.) in DMEM (Sigma, Milan, Italy) supplemented with 10% foetal bovine serum (FBS), 1% non-essential amino acids and antibiotics. The cells were divided 1:2 at one-week intervals and used between the third and fourth passage. Cells from confluent cultures of MSC were detached using 0.25% trypsin in 1 ml MEDTA and plated in triplicate at a density of $5\times10^4$ and $1\times10^4$ cells/cm², respectively, on the granulated powders to be tested and 24-well polystyrene plates as a control.

The plate cultures were incubated at 37° C. for 7 days. After incubation, the culture medium was removed; 200 µl of MTT (colorimetric test 3-dimethylthiazol-2,5-diphenyltetrazolium bromide Aldrich 135038) and 1.8 ml of the culture medium was added to the individual cell monolayers; the multilayer plates were incubated at 37° C. for another 3 hours.

After separation of the surnatant, the blue formazan crystals were dissolved by adding 2 ml of solvent (4% HCl 1N in absolute isopropanol) and spectrophotometrically quantified at 570 nm.

With respect to stoichiometric HA, the magnetic HA powders represent a suitable substrate in terms of cell adhesion and proliferation for osteoblast precursors (MSC).

The MTT value is 80% for magnetic HA whereas for HA it is 82%6. The SEM morphological analyses conducted on cultured cells showed a good biocompatibility of the MSC with all the powders tested. Similarly to their behaviour on HA, on magnetic HA the cells showed a diffuse "stretched out" morphology, with a number of cytoplasmic extensions in contact with the powder.

In conclusion, the simultaneous addition of $FeCl_2$ and $FeCl_3$ as sources of ions for partially substituting the calcium in the HA lattice and the use of optimized synthesis parameters made it possible to obtain $Fe^{3+}/Fe^{2+}$ substituted HA having an $Fe^{3+}/Fe^{2+}$ ratio equal to about 3 and an $(Fe_+Ca)/P$ ratio very close to the theoretical one.

Using XRD and computer simulations on structural models, a clear indication is obtained that both species of Fe are in calcium substitution positions and not at interstitial sites in the HA lattice.

The Ca(2) position, with a coordination number of 6, and Ca(1) position, with a coordination number of 4, are occupied in a reciprocal relationship in such a way as to impart magnetic susceptibility to the powders, thanks to strictly defined synthesis parameters.

The TEM investigations, as well as the magnetic measurements, confirm the presence of a new magnetic phase of HA together with nanoclusters similar to magnetite.

This new phase is a distorted/disordered hydroxyapatite with $Fe^{2+}$, in its nominal divalent state, and $Fe^{3+}$, which has a deviation from its nominal trivalent state, organized on a surface and bulk level and coordinated to generate magnetism in the HA itself.

These results, together with the biocompatibility of the magnetic HA, provide regenerative medicine with a new family of biocompatible biomimetic materials that can be controlled and manipulated through suitable external magnetic fields; these materials can in fact be employed for the purpose of producing 1) nanoparticles for carrying and releasing bioactive factors and/or drugs, 2) nanoparticles usable for diagnostic (imaging) and treatment (hyperthermia) purposes, 3) bone or osteocartilage substitutes which can be biologically manipulated in situ (i.e. 'reloaded' or in any case stimulated after implantation in vivo, with specific factors according to the quali-quantitative and time requirements of the patient) and even fixed in a given position in vivo (eliminating reliance on traditional fixing systems).

The invention claimed is:

1. A hydroxyapatite comprising calcium ions and phosphate ions in a crystal lattice, characterized in that it is doped with $Fe^{2+}$ ions and $Fe^{3+}$ ions, said $Fe^{2+}$ and said $Fe^{3+}$ being inside said crystal lattice and partially substituting said calcium ions in said crystal lattice in a quantitative ratio $Fe^{3+}/Fe^{2+}$ of 1 to 4, has magnetism of 0.05 to 8 emu/g, measured by applying a magnetic field of 34 Oe, due to the presence of magnetic nano-domains in the lattice of hydroxyapatite, and comprises an amount of secondary magnetic phases below about 3 vol %.

2. The hydroxyapatite according to claim 1, wherein said magnetism is of 0.1 to 5 emu/g, recorded by applying a magnetic field of 34 Oe.

3. The hydroxyapatite according to claim 1 or 2, wherein said ratio $Fe^{3+}/Fe^{2+}$ is of 2 to 3.5.

4. The hydroxyapatite according to claim 1, comprising an amount of secondary magnetic phases≤2 vol %.

5. The hydroxyapatite according to claim 1, having a ratio (Fe+Ca)/P of 1.5 to 1.9.

6. The hydroxyapatite according to claim 1, in the form of nanoparticles having a width of 5-30 nm and a length up to 150 nm, or in the form of aggregates of said nanoparticles.

7. The hydroxyapatite according to claim 6, wherein said nanoparticles comprise spherical voids of 2-5 nm.

8. The hydroxyapatite according to claim 1, loaded with biological substances selected in the group consisting of proteins, genes, stem cells, growth factors and vascularization factors.

9. A biomimetic bone or osteocartilage substitute comprising a hydroxyapatite according to claim 1.

10. A method of treating or diagnosis a medical condition comprising the steps of providing the hydroxyapatite according to claim 1 and loading the hydroxyapatite with one or more biological substances or drugs and using the loaded hydroxyapatite as a carrier and release agent for said one or more biological substances or drugs or as a contrast agent for diagnosis or as material for bone or osteocartilage regeneration.

11. The method according to claim 10, wherein said loaded hydroxyapatite is used as a carrier and release agent for said one or more biological substances or drugs.

12. The method according to claim 10, wherein said loaded hydroxyapatite is used as a contrast agent in diagnostics.

13. The method according to claim 10, wherein said loaded hydroxyapatite is use as a material for bone or osteocartilage regeneration.

14. A method for preparing the hydroxyapatite according to claim 1, comprising the following steps:
 a) adding a solution comprising Fe(II) and Fe(III) ions to a suspension/solution containing Ca(II) ions;
 b) adding a solution of phosphate ions to the suspension/solution of step a);
 c) heating the suspension/solution of step b) to a temperature of 15° to 80° C.;
 d) separating a precipitate from mother liquors obtained in step c) to obtain the hydroxyapatite according to claim 1.

15. A method according to claim 14, wherein said solution of phosphate ions is added to the suspension/solution containing Ca(II) ions and iron ions in a period of 1-3 hours.

16. A method according to claim 14, wherein after adding phosphate ions, the ratio of iron ions with respect to calcium ions is adjusted by further adding of a solution of iron ions so as to obtain a molar ratio Fe/Ca of 5 to 30mol %.

17. A method according to claim 14, wherein said Fe(II) and Fe(III) ions derive from $FeCl_2$ and $FeCl_3$, respectively.

18. A method according to claim 14, wherein said Ca(II) ions derive from calcium hydroxide, calcium nitrate, calcium acetate, calcium carbonate or combinations thereof.

19. A method according to claim 14, wherein said phosphate ions derive from phosphoric acid.

20. The hydroxyapatite according to claim 1, loaded with active substances or drugs.

21. The hydroxypatatite according to claim 1, in a form of nanoparticles having a width of 10-20 nm.

22. The hydroxyapatite according to claim 1, in a form of nanoparticles having a length of 80-150 nm.

* * * * *